(12) United States Patent
Huang et al.

(10) Patent No.: US 10,918,675 B2
(45) Date of Patent: Feb. 16, 2021

(54) WATER RESISTANT ENHANCED WOUND HEALING FILM AND PREPARATION METHOD THEREOF

(71) Applicant: HUAZHONG AGRICULTURAL UNIVERSITY, Hubei (CN)

(72) Inventors: Xi Huang, Hubei (CN); Xiaoyun Li, Hubei (CN); Meihu Ma, Hubei (CN); Zhaoxia Cai, Hubei (CN); Xing Fu, Hubei (CN)

(73) Assignee: HUAZHONG AGRICULTURAL UNIVERSITY, Wuhan (CN)

( * ) Notice: Subject to any disclaimer, the term of this patent is extended or adjusted under 35 U.S.C. 154(b) by 69 days.

(21) Appl. No.: 16/173,153

(22) Filed: Oct. 29, 2018

(65) Prior Publication Data

US 2020/0030385 A1 Jan. 30, 2020

(30) Foreign Application Priority Data

Jul. 26, 2018 (CN) .......................... 201810837007.7

(51) Int. Cl.
| | |
|---|---|
| *A61L 15/32* | (2006.01) |
| *A61K 35/57* | (2015.01) |
| *A61P 17/02* | (2006.01) |
| *A61K 9/70* | (2006.01) |
| *A61K 38/47* | (2006.01) |
| *A61K 47/10* | (2017.01) |
| *A61K 47/38* | (2006.01) |

(52) U.S. Cl.
CPC ............ *A61K 35/57* (2013.01); *A61K 9/7007* (2013.01); *A61K 38/47* (2013.01); *A61K 47/10* (2013.01); *A61K 47/38* (2013.01); *A61P 17/02* (2018.01)

(58) Field of Classification Search
CPC .................................................... A61L 15/32
See application file for complete search history.

(56) References Cited

PUBLICATIONS

English translation of Yue, CN 1887295 A, 2007.*
English translation of Masahiro et al., WO 2004/005607 A1, 2004.*
English translation of Cui, CN 103656734 A, 2014.*

* cited by examiner

*Primary Examiner* — Rosanne Kosson

(57) ABSTRACT

A water resistant enhanced wound healing film includes components by mass volume concentration of: 5-10 mg/L of ultra-fine eggshell powder, 50-500 mg/L of ultramicroshell membrane powder or shell membrane soluble protein, 5-30 mg/L of lysozyme, 5-10 mg/L of chitosan, 0.05-5 mg/L of glycerin, and 0.1-5 mg/L of polymer polysaccharide. Also, a preparation method of the water resistant enhanced wound healing film is disclosed. The whole raw materials of the present invention are non-toxic and have good biocompatibility; the raw materials include eggshell, shell membrane and soluble mixed protein thereof, and lysozyme in residual egg white. In the present invention, various components of the eggshell waste are sufficiently used. The wound healing film has good water resistance, mechanical properties, antibacterial activity and protein absorption capacity, and low degradation rate. The method of the present invention has simple process, strong practicability, extremely low production cost, favorable resource recycling and low energy consumption.

12 Claims, 5 Drawing Sheets

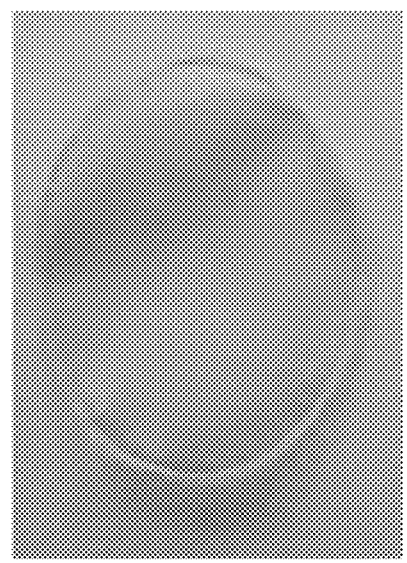
Fig. 2a                     Fig. 2b
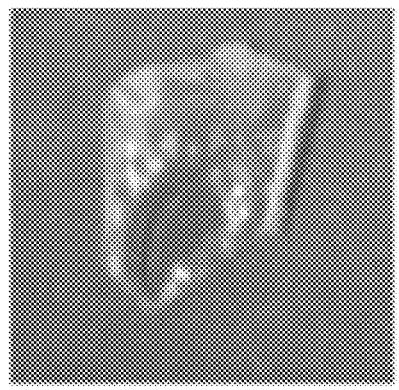
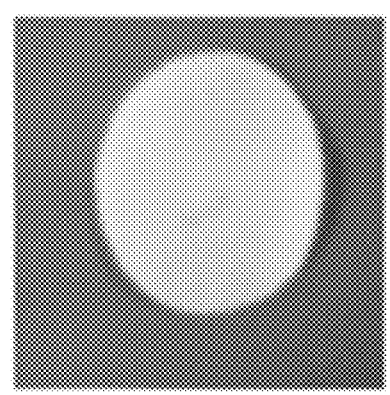
Fig. 3-1a                   Fig. 3-1b
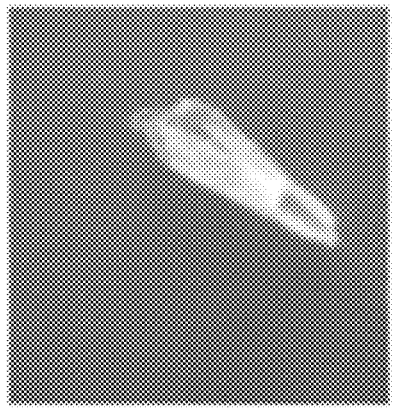
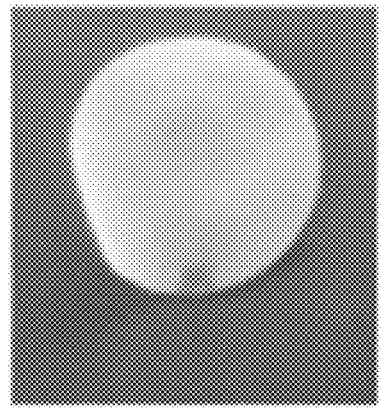
Fig. 3-2a                   Fig. 3-2b

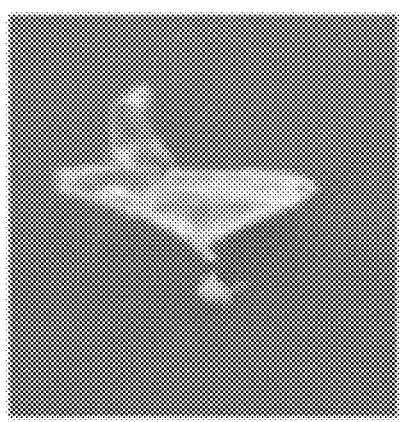 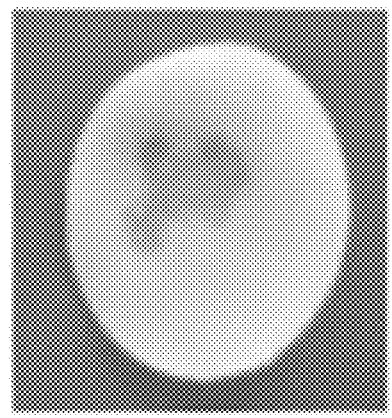
Fig. 3-3a  Fig. 3-3b
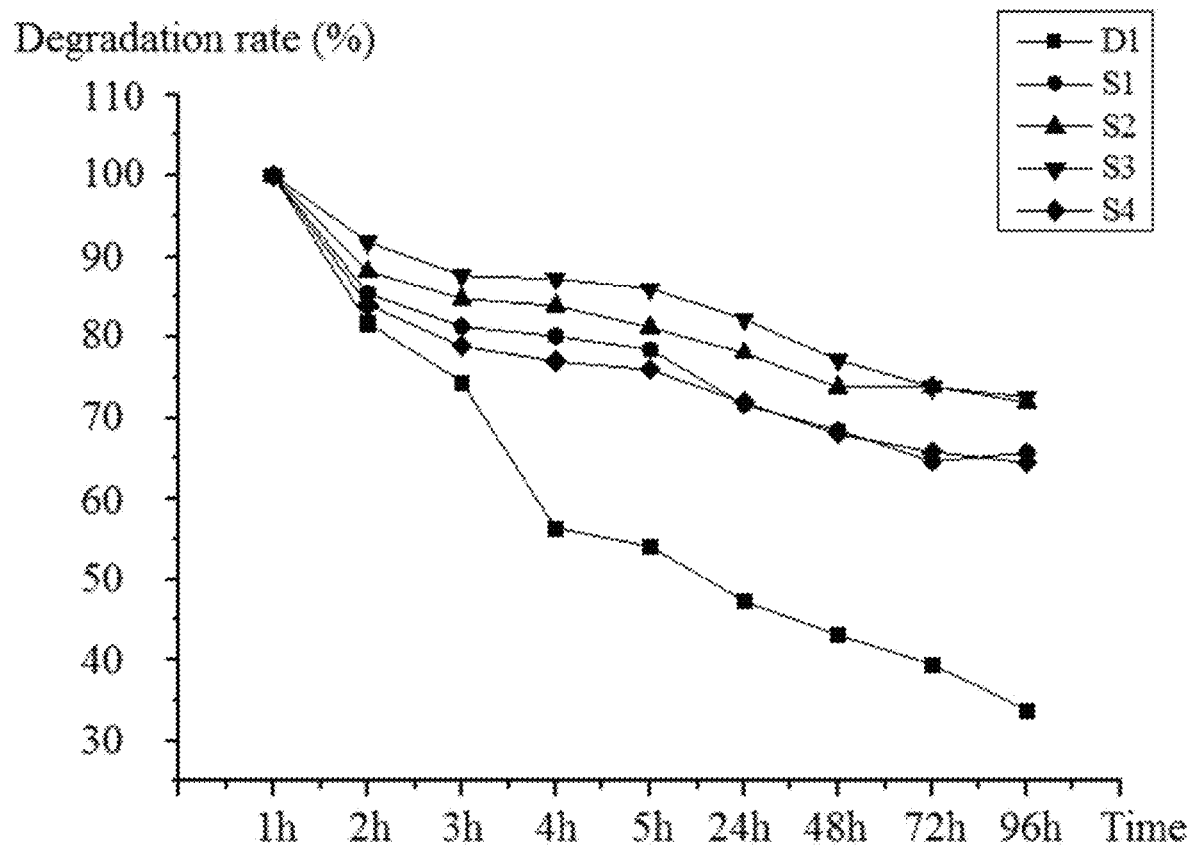
Fig. 4

WATER RESISTANT ENHANCED WOUND HEALING FILM AND PREPARATION METHOD THEREOF

CROSS REFERENCE OF RELATED APPLICATION

The present invention claims priority under 35 U.S.C. 119(a-d) to CN 201810837007.7, filed Jul. 26, 2018.

BACKGROUND OF THE PRESENT INVENTION

Field of Invention

The present invention relates to a water resistant enhanced wound healing film and a preparation method thereof, and more particularly to a water resistant enhanced wound healing film and a preparation method of the water resistant enhanced wound healing film which uses high-molecular polymer, chitosan and an eggshell membrane as raw materials.

Description of Related Arts

As the most important country for the consumption and processing of poultry eggs, China has ranked first in the world in terms of per capita possession for more than 20 years. In order to meet the multi-level needs of consumers for egg products, many large egg processing companies have flourished. However, at present, these enterprises mainly use primary or deep processing technology to make egg contents (egg white and egg yolk) into egg liquid or egg powder, and the use of eggshell and eggshell membranes is relatively small, most of eggshell resources are only treated as waste, resulting in a large amount of waste of resources. From the perspective of environmental protection and resource reuse, domestic and foreign scholars have done a lot of research on eggshells.

In fact, the discarded eggshell (the discarded eggshell with residual egg white) has a variety of functional active ingredients, such as the rich calcium carbonate in the eggshell, which is a good mineralization product. Eggshell membrane, commonly known as "phoenix clothing", is located between egg white and eggshell. It consists of 2 μm fibers and has a network structure. The mesh diameter of the eggshell membrane is 4 μm on average and the thickness thereof is mostly in a range of 65-69 μm. The eggshell membrane contains 90% of high molecular protein which is mainly in the form of glycoproteins and includes collagen, elastin, keratin, lysozyme, sialic glycoprotein, hyaluronic acid, ovalbumin, chondroitin sulfate and sialic acid osteopontin (OPN); and moreover, the eggshell membrane also contains about 3% of liposomes and 2% of saccharides. The eggshell membrane is a natural biomaterial due to a natural bioactive matrix structure. At present, the utilization of eggshell membranes is mainly in the form of shell membrane particles and soluble shell membrane proteins. The eggshell membrane itself has a certain inhibiting effect on microbial growth. More than 400 years ago, China used the shell membrane in the treatment of wounds. This phenomenon has been recorded in the pharmacopoeia. In Japan, current sumo athletes still use the shell membrane to heal the wound.

During the egg-breaking process, part of egg white will remain on the inner surface of the shell membrane. During the actual application or recycling process, the residual egg white is often washed away. In fact, the residual egg white contains a variety of active proteins, such as lysozyme and transferrin, so it can be used after simple processing, which has important practical significance for improving the comprehensive utilization value of eggs. Since the waste eggshell has many biological functional activities, it is a hot topic at home and abroad to prepare corresponding biological functional materials by using the shell membrane as the research object.

Chitosan is a macromolecular polymer with good biocompatibility, film formation, non-toxicity, hemostasis and bacteriostatic properties. In skin tissue engineering, since chitosan has a constituent substance similar to glycoprotein (GAG) in human cell matrix, it is often prepared as a biomaterial that promotes wound healing and cell proliferation. Due to the above physical and chemical properties, chitosan is prepared into various forms of biologically functional materials such as hemostatic sponges, wound healing films and wound healing hydrogels.

Wound healing is a complex process. In the process of wound healing, the process of wound healing is often accelerated by avoiding the wound being infected by external microorganisms, absorbing excessive wound exudate or stopping bleeding. At present, a good wound healing dressing should have the characteristics of bacteriostatic or hemostasis effect. In addition, the wound healing dressing should also have good strength, water resistance and mechanical properties.

At present, there are many research literatures on the recycling of eggshells or eggshell membranes published at home and abroad. For example, Chinese patent No. CN 103898016A relates to a method for fermenting lactic acid bacteria by eggshells; Chinese patent No. CN 107871614A discloses a method for preparing a dye-sensitized solar cell with eggshell membranes; Chinese patent No. CN 105919909A utilizes an eggshell membrane to prepare a water-soluble antioxidant health care product. The above patents or patent applications have successfully increased the added value of waste, but these patents mainly use one of the eggshell wastes (eggshell or eggshell membrane) for utilization, ignore the comprehensive utilization of eggshell wastes. And most patents or patent applications have never used the egg white remaining on the surface of the egg membrane. These studies have not improved the recovery of eggshell wastes to a greater extent.

There are many researches on the preparation of healing wound dressings with high molecular polymer chitosan. The patent number CN 106215232 discloses that a silk fibroin raw material, a bioactive glass raw material, a chitosan raw material and a polyvinyl alcohol raw material are mixed according to a certain ratio, and then freeze-dried into a cream for healing wounds. The patent number CN 107281268A discloses that various non-toxic raw materials such as chitosan, asarum, myrrh, white peony, trichosanthin, chinese toona root-bark, blood charcoal, trogopterus dung, mint, pumpkin seed and frankincense are mixed and dried to form chitosan thermosensitive gel particles to promote wound healing. The document of the patent number CN 107080856A relates to a method for preparing a wound healing film, which comprises compounding bacterial cellulose, chitosan, and lithium algae, and forming a three-dimensional nanofiber network by physically crosslinking. The document of the patent number CN 107080856A relates to a liquid dressing that can be applied to a wound, in which glycosylated chitosan and an aloe extract are mixed according to a certain ratio. The above patents or patent applications mostly use chitosan as the research object, which proves the feasibility of preparing wound healing dressings based on chitosan. However, due to the weak mechanical properties of chitosan film, it is easy to melt and degrade in water, and has very weak water resistance, which limits the preparation of wound healing dressing with a single chitosan. The defects of chitosan are compensated from the above patents or patent applications or by fibrillating chitosan or mixing with other various raw materials. Moreover, the preparation method of the dressing is too complicated, the raw material objects are diversified, or the applied technology limits the large-scale promotion in industry or life.

In the preparation process, the membrane often needs to be crosslinked by adding some crosslinking agents to improve the mechanical properties of the membrane. However, some commonly used crosslinking agents (such as glutaraldehyde) have certain toxic effects, which limits the use of membranes in bioengineering and other fields. Calcium chloride, as a natural non-toxic physical crosslinking agent, has clearly become a novel crosslinking agent for the preparation of membranes or gels. The document of the patent number CN 105457094A relates to a method for preparing a sodium alginate nanofiber scaffold material using calcium chloride as a crosslinking agent. The document of the patent number CN 107619487A relates to a method for preparing an alginate electric drive film using calcium chloride as a crosslinking agent. The document of the patent number CN 106832687A relates to a method for preparing a hollow calcium carbonate crosslinked low-cost lightweight cable material. The above patents or patent applications mostly use calcium chloride as a crosslinking agent to prove the feasibility of calcium chloride crosslinked chitosan film.

In addition, China Patent No. CN 107106733A discloses a micronized shell membrane powder for healing wounds, which merely discloses that the micronized shell membrane powder has a healing wound effect, but does not relate to the form in which the shell membrane powder should be applied to the wound for avoiding secondary damage to the wound. No patent application for preparing wound healing materials using poultry eggshell membrane soluble protein as raw material has been found. At the same time, although China patent No. CN 1107043798A discloses a method for recycling eggshells, wherein under a condition that eggshell membrane and eggshell are not completely separated, biologically active components thereof are respectively extracted. CN 1107043798A has better innovativeness, but does not disclose the use of functional activity of eggshell membranes and eggshells.

The present invention provides a method for preparing a water resistant enhanced wound healing film by using a high molecular polymer, an eggshell membrane and chitosan as raw materials.

SUMMARY OF THE PRESENT INVENTION

A technical problem to be solved of the present invention is to provide a water resistant enhanced wound healing film and a preparation method thereof, wherein the water resistant enhanced wound healing film is prepared by using high-molecular polymer, chitosan and an eggshell membrane as raw materials.

To solve the above technical problem, the present invention provides technical solutions as follows.

The present invention provides a water resistant enhanced wound healing film which comprises components by mass volume concentration of:

| | |
|---|---|
| ultra-fine eggshell powder | 5-10 mg/L; |
| ultramicroshell membrane powder or shell membrane soluble protein | 50-500 mg/L; |
| lysozyme | 5-30 mg/L; |
| chitosan | 5-10 mg/L; |
| glycerin and | 0.05-5 mg/L; |
| polymer polysaccharide | 0.1-5 mg/L. |

Further, the ultra-fine eggshell powder is made from chicken eggs, duck eggs, quail eggs or goose eggs.

Further, the ultramicroshell membrane powder or shell membrane soluble protein is made from chicken eggs, duck eggs, quail eggs or goose eggs.

Further, a particle size of the ultra-fine eggshell powder is in a range of 10 to 1000 nm.

Further, a particle size of the ultramicroshell membrane powder is in a range of 10 to 1000 nm.

Also, the present invention provides a preparation method of the water resistant enhanced wound healing film, which uses ultra-fine eggshell powder, ultramicroshell membrane powder or shell membrane soluble protein, lysozyme extracted from residual egg white, and chitosan as raw materials, wherein the water resistant enhanced wound healing film comprises components by mass volume concentration of:

| | |
|---|---|
| ultra-fine eggshell powder | 5-10 mg/L; |
| ultramicroshell membrane powder or shell membrane soluble protein | 50-500 mg/L; |
| lysozyme | 5-30 mg/L; |
| chitosan | 5-10 mg/L; |
| glycerin and | 0.05-5 mg/L; |
| polymer polysaccharide | 0.1-5 mg/L. |

Further, the preparation method comprises steps of:

(S1) selecting a fresh egg, cleaning a surface of the fresh egg, removing a content of the fresh egg, and obtaining an eggshell with membrane containing egg white residues;

(S2) washing the eggshell with the membrane containing the egg white residues with a first amount of deionized water, and respectively collecting the eggshell with the membrane and an aqueous solution containing the egg white residues;

(S3) adjusting a pH (potential of hydrogen) value of the aqueous solution containing the egg white residues collected by the step of (S2) in a range of 6-12 with acid or alkali, extracting by adsorption resin, and obtaining lysozyme;

(S4) drying the eggshell with the membrane collected by the step of (S2), preliminarily smashing with a pulverizer, immersing in a second amount of deionized water, stirring and mechanically separating the eggshell from the membrane, respectively collecting the eggshell and the membrane according different densities, superfine grinding the eggshell and the membrane, and obtaining ultra-fine eggshell powder and ultramicroshell membrane powder;

(S5) extracting a soluble mixed protein in the ultramicroshell membrane powder by using any one of mercaptopropionic acid, thioglycolic acid and acetic acid as a solvent, freeze-drying, and obtaining shell membrane soluble protein powder;

(S6) mixing the lysozyme obtained by the step of (S3) and a chitosan acetic acid solution with a concentration in a range of 1-5 mg/L according to a proportion of adding 5 mg to 30 mg of the lysozyme per 1 L of the chitosan acetic acid solution, evenly stirring, and obtaining a first mixed liquid containing lysozyme and chitosan;

(S7) mixing the ultra-fine eggshell powder obtained by the step of (S4) and the first mixed liquid obtained by the step of (S6) according to a proportion of adding 5 mg to 30 mg of the ultra-fine eggshell powder per 1 L of the first mixed liquid, evenly stirring, and obtaining a second mixed liquid containing eggshell powder, lysozyme and chitosan;

(S8) mixing the ultramicroshell membrane powder obtained by the step of (S4) or the shell membrane soluble protein powder obtained by the step of (S5) with the second mixed liquid obtained by the step of (S7) according to a proportion of adding 50 mg to 500 mg of the ultramicroshell membrane powder or the shell membrane soluble protein powder per 1 L of the second mixed liquid, evenly stirring, obtaining a first mixture, adding glycerin 0.05% to 5% volume percentage of the first mixture and polymer polysaccharide 0.1% to 5% volume percentage of the first mixture into the first mixture, evenly stirring, and obtaining a mixed solution;

(S9) taking the mixed solution obtained by the step of (S8), evenly dispersing the ultramicroshell membrane powder or the shell membrane soluble protein powder in the mixed solution under a ultrasound condition, and obtaining a suspension liquid; and (S10) adding 1.5 mL of the suspension liquid obtained by the step of (S9) into a well plate, laying horizontally, drying at a temperature in a range of 25 to 50° C., obtaining a film, removing the film from the well plate, drying and storing, and obtaining the water resistant enhanced wound healing film.

Preferably, the alkali in the step of (S3) for adjusting the pH value is sodium hydroxide or potassium hydroxide.

Preferably, the adsorption resin in the step of (S3) is at least one resin selected from a group consisting of D152 cation exchange resin, FPC3500 cation exchange resin and AB-8 cation exchange resin, an add amount of the adsorption resin is 0.1%-20% w/v.

Preferably, in the step of (S8), the polymer polysaccharide is at least one member selected from a group consisting of carboxymethyl cellulose, xanthan gum and dextran.

Preferably, in the step of (S4), the eggshell is mechanically separated from the membrane at a rotational speed in a range of 2000 to 6000 rpm/min for 2-4 h.

Preferably, in the step of (S6), the first mixed liquid is obtained by stirring in a magnetic stirrer for 6-15 h.

Preferably, in the step of (S7), the second mixed liquid is obtained by stirring at a rotational speed in a range of 2000 to 5000 rpm/min for 1-5 h.

Preferably, in the step of (S9), the ultrasound condition is continuous ultrasound or intermittent ultrasound with an ultrasonic intensity in a range of 100 to 400 W and an ultrasonic time in a range of 30 to 60 min.

Beneficially effects of the present invention are as follows.

(1) The present invention can comprehensively utilize the egg white remaining in the shell membrane to the recycle and reuse of the eggshell, so as to increase the recovery rate of the eggshell and increase the added value of shell membrane waste to a large extent.

(2) The present invention can also better overcome the defect of using chitosan as a healing wound dressing film. In the prior art, chitosan is used as a wound healing dressing, and more bioactive substances or other cross-linking agents are often added in the preparation process of the wound healing dressing film to increase the water resistance of chitosan, which causes cumbersome process and increased cost; and furthermore, the crosslinking agent has a certain toxic effect. The present invention creatively adds the waste eggshell powder into the mixed solution of the high molecular polymer, and under an acidic condition (chitosan acetic acid solution), the formed calcium ions can be used as a natural non-toxic crosslinking agent, and the physical crosslinking characteristics of calcium ions in eggshell is utilized to overcome the defect of poor water resistance of chitosan film. As a result, the water resistance and the mechanical property of the composite film in water are enhanced, and the composite degradation rate of the composite film is improved, so that the technical defects in the prior art are successfully solved.

(3) Compared with the prior art, the raw materials adopted by the present invention are non-toxic and have good biocompatibility.

(4) The present invention can realize a combination of a plurality of high molecular polymers, including a shell membrane and a soluble mixed protein thereof (oxidation resistance and antibacterial activity), lysozyme (antibacterial activity) and chitosan (film-forming property, biocompatibility and antibacterial activity) to successfully prepare a water resistant enhanced wound healing film. The combination of the plurality of high molecular polymers, including shell membrane and its soluble mixed protein, lysozyme and chitosan, makes all ingredients of eggshell waste are sufficiently utilized.

(5) The present invention uses high molecular polymer, eggshell membranes and chitosan as raw materials to prepare the wound healing film. Compared with the film prepared by using simple chitosan as a raw material, the present invention has advantages as follows.

(a) The wound healing film provided by the present invention has a certain water resistance and mechanical properties. For example, after being immersed in wound simulated liquid (salt saline) for 1 to 3 days, the wound healing film provided by the present invention still have a complete appearance.

(b) The wound healing film provided by the present invention has good physical appearance, such as good flexibility, folding resistance and transparency.

(c) The wound healing film provided by the present invention has good protein absorption capacity. For example, bovine serum albumin absorption rate is in a range of 60 mg/g-80 mg/g which is significantly higher than the simple chitosan absorption rate of 40 mg/g.

(d) The wound healing film provided by the present invention can greatly reduce the degradation rate of the dressing and shorten the healing time of the dressing.

(e) The wound healing film provided by the present invention provides a suitable pH for rapid wound healing and creates a microenvironment for wound healing.

(f) The wound healing film provided by the present invention can significantly inhibit the growth of *Escherichia coli* and *Staphylococcus aureus*. By inhibiting the growth of microorganisms, the dressing can effectively prevent the microorganisms from infecting wounds so as to improve the speed of wound healing.

In summary, the preparation method provided by the present invention not only has superior performance in the prepared wound healing film, but also has simple process, strong practicability, low production cost, favorable resource recycling, low energy consumption, no involvement of toxic or corrosive substances throughout the preparation process, and no pollution to the environment, so that the added value of by-products of poultry egg processing is greatly improved, resulting in significant economic and social benefits.

BRIEF DESCRIPTION OF THE DRAWINGS

In order to more clearly illustrate technical solutions of embodiments of the present invention, the drawings used in the embodiments will be briefly described as below. It should be understood that the following drawings show only certain embodiments of the present invention and are therefore not considered as limiting the protective scope of the present invention. For those skilled in the art, other relevant drawings can also be obtained according to these drawings without any creative work.

FIG. 2a is an appearance pattern of a simple chitosan film sample D1 in a comparative example after being immersed in a wound simulating fluid for 24 h.

FIG. 2b is an appearance pattern of a water resistant enhanced wound healing film sample S3 after being immersed in a wound simulating fluid for 24 h provided by the present invention.

FIGS. 3-1a and 3-1b are two appearance patterns of the simple chitosan film sample D1 in the comparative example and the water resistant enhanced wound healing film sample S3 provided by the present invention after being immersed in normal saline for 1 day, respectively.

FIGS. 3-2a and 3-2b are two appearance patterns of the simple chitosan film sample D1 in the comparative example and the water resistant enhanced wound healing film sample S3 provided by the present invention after being immersed in normal saline for 2 days, respectively.

FIGS. 3-3a and 3-3b are two appearance patterns of the simple chitosan film sample D1 in the comparative example and the water resistant enhanced wound healing film sample S3 provided by the present invention after being immersed in normal saline for 3 days, respectively.

FIG. 4 is a curve graph of degradation rate changing with time of the simple chitosan film sample D1 in the comparative example and the water resistant enhanced wound healing film samples S1-S4 provided by the present invention.

DETAILED DESCRIPTION OF THE PREFERRED EMBODIMENT

In order to be understood by those skilled in the art, the present invention will be further described in detail with reference to accompanying drawings and embodiments as follows.

First Embodiment

Figure 1:
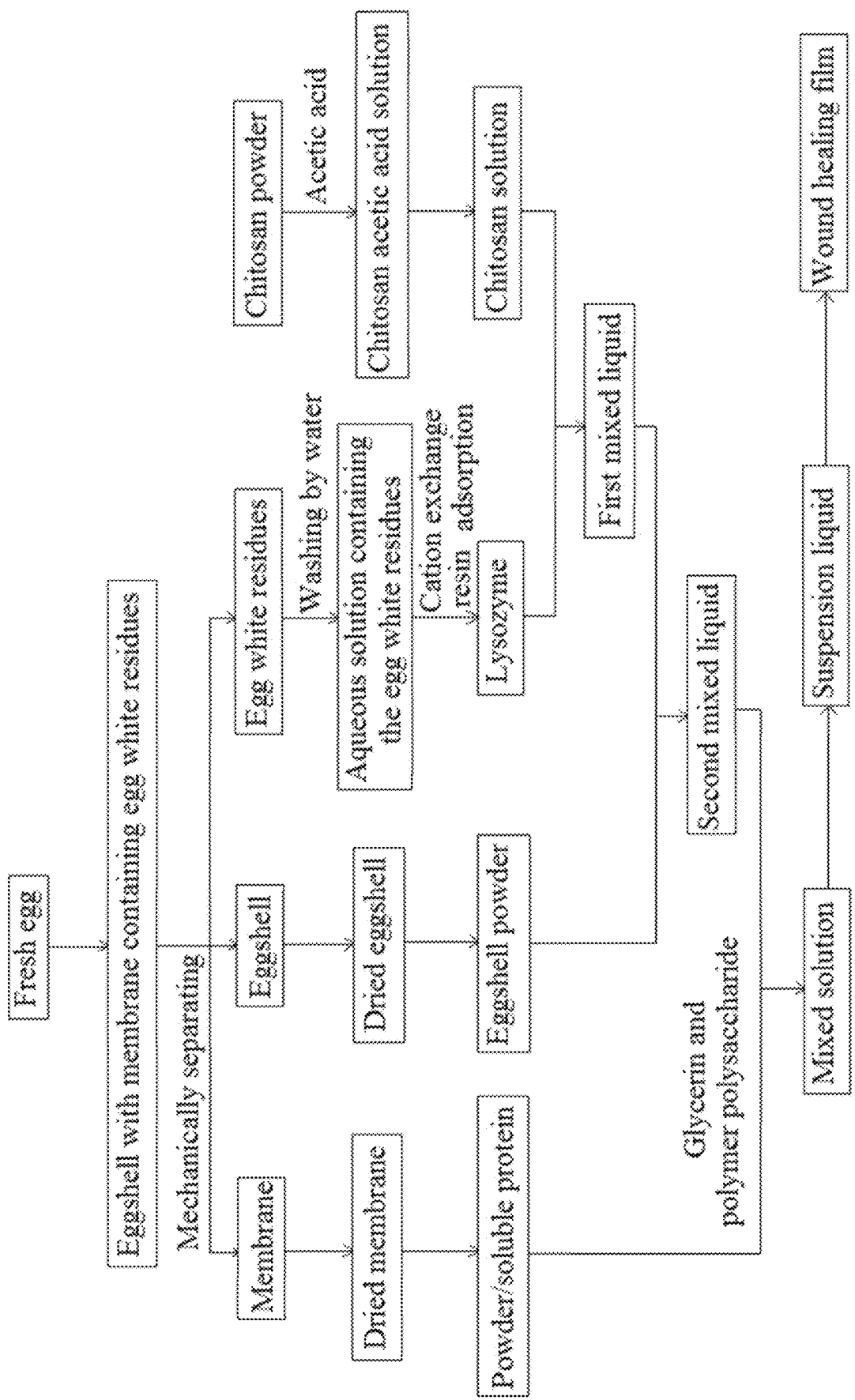
FIG. 1 is a flow chart of a preparation method of a water resistant enhanced wound healing film provided by the present invention.

As shown in FIG. 1, a preparation method of a water resistant enhanced wound healing film according to a first embodiment of the present invention is illustrated, wherein the water resistant enhanced wound healing film is prepared by using high-molecular polymer, chitosan and eggshell membrane as raw materials. The preparation method comprises steps of:

(S1) selecting a fresh egg, cleaning a surface of the fresh egg, removing a content of the fresh egg, and obtaining an eggshell with membrane containing egg white residues;

(S2) washing the eggshell with the membrane containing the egg white residues with a first amount of deionized water according to a proportion of adding 1 mg of the eggshell with the membrane containing the egg white residues per 2 mL of the first amount of deionized water, and respectively collecting the eggshell with the membrane and an aqueous solution containing the egg white residues;

(S3) adjusting a pH (potential of hydrogen) value of the aqueous solution containing the egg white residues collected by the step of (S2) to 6 by NaOH (sodium hydroxide) solution with a concentration of 1 mol/L, and then adding 0.1% of D152-type cation exchange resin, and extracting lysozyme by resin adsorption;

(S4) preliminarily smashing with a pulverizer after drying the eggshell with the membrane collected by the step of (S2), immersing in a second amount of deionized water, mechanically stirring under a rotational speed of 2000 rpm/min for 2 h, standing for 15 min, suspending the membrane in an aqueous phase, sinking the eggshell at a bottom of a beaker due to large density of the eggshell, drying at 50° C. for 24 h after respectively collecting the eggshell and the membrane, respectively ball-milling the eggshell and the membrane into ultrafine powder with a same bore diameter of 100 nm by a ball mill, and respectively obtaining ultra-fine eggshell powder and ultramicroshell membrane powder;

(S5) extracting a soluble mixed protein in the ultramicroshell membrane powder by using acetic acid as a solvent, freeze-drying, and obtaining shell membrane soluble protein powder;

(S6) mixing the lysozyme obtained by the step of (S3) and a chitosan acetic acid solution with a concentration of 1 mg/L according to a proportion of adding 5 mg of the lysozyme per 1 L of the chitosan acetic acid solution, evenly stirring for 10 h in a magnetic stirrer, standing for a period of time, defoaming and obtaining a first mixed liquid containing lysozyme and chitosan;

(S7) mixing the ultra-fine eggshell powder obtained by the step of (S4) and the first mixed liquid obtained by the step of (S6) according to a proportion of adding 5 mg of the ultra-fine eggshell powder per 1 L of the first mixed liquid, evenly stirring for 4 h under a rotational speed of 2000 rpm/min, mixing and obtaining a second mixed liquid containing eggshell powder, lysozyme and chitosan;

(S8) mixing the ultramicroshell membrane powder obtained by the step of (S4) or the shell membrane soluble protein powder obtained by the step of (S5) with the second mixed liquid obtained by the step of (S7) according to a proportion of adding 50 mg of the ultramicroshell membrane powder or the shell membrane soluble protein powder per 1 L of the second mixed liquid, evenly stirring, obtaining a first mixture, adding glycerin 1% volume percentage of the first mixture and polymer polysaccharide 2% volume percentage of the first mixture into the first mixture, magnetically stirring for 2 h under a rotational speed of 3500 rpm/min, evenly mixing and obtaining a mixed solution;

(S9) taking 50 mL of the mixed solution obtained by the step of (S8), evenly dispersing the ultrafine membrane powder or the membrane soluble protein powder in the mixed solution under a continuous ultrasound condition with an intensity of 100 W for 60 min, and obtaining a suspension liquid; and (S10) adding 0.75 mL of the suspension liquid obtained by the step of (S9) into a 12-well plate, horizontally laying, drying at a temperature of 37° C., obtaining a film on the 12-well plate, removing the film from the 12-well plate, storing in a dryer, and obtaining the water resistant enhanced wound healing film and recording as a sample S1.

Second Embodiment

As shown in FIG. 1, a preparation method of a water resistant enhanced wound healing film according to a second embodiment of the present invention is illustrated, wherein the water resistant enhanced wound healing film is prepared by using high-molecular polymer, chitosan and eggshell membrane as raw materials. The preparation method comprises steps of:

(S1) selecting a fresh egg, cleaning a surface of the fresh egg, removing a content of the fresh egg, and obtaining an eggshell with membrane containing egg white residues;

(S2) washing the eggshell with the membrane containing the egg white residues with a first amount of deionized water according to a proportion of adding 1 mg of the eggshell with the membrane containing the egg white residues per 5 L of the first amount of deionized water, and respectively collecting the eggshell with the membrane and an aqueous solution containing the egg white residues;

(S3) adjusting a pH (potential of hydrogen) value of the aqueous solution containing the egg white residues collected by the step of (S2) to 8 by NaOH (sodium hydroxide) solution with a concentration of 1 mol/L, and then adding 3% of D152-type cation exchange resin, and extracting lysozyme by resin adsorption;

(S4) preliminarily smashing with a pulverizer after drying the eggshell with the membrane collected by the step of (S2), immersing in a second amount of deionized water, mechanically stirring under a rotational speed of 6000 rpm/min for 4 h, standing for 15 min, suspending the membrane in an aqueous phase, sinking the eggshell at a bottom of a beaker due to large density of the eggshell, drying at 50° C. for 24 h after respectively collecting the eggshell and the membrane, respectively ball-milling the eggshell and the membrane into ultrafine powder with a same bore diameter of 100 nm by a ball mill, and respectively obtaining ultra-fine eggshell powder and ultramicroshell membrane powder;

(S5) extracting a soluble mixed protein in the ultramicroshell membrane powder by using mercaptopropionic acid as a solvent, freeze-drying, and obtaining shell membrane soluble protein powder;

(S6) mixing the lysozyme obtained by the step of (S3) and a chitosan acetic acid solution with a concentration of 1 mg/L according to a proportion of adding 10 mg of the lysozyme per 1 L of the chitosan acetic acid solution, evenly stirring for 10 h in a magnetic stirrer, standing for a period of time, defoaming and obtaining a first mixed liquid containing lysozyme and chitosan;

(S7) mixing the ultra-fine eggshell powder obtained by the step of (S4) and the first mixed liquid obtained by the step of (S6) according to a proportion of adding 7 mg of the ultra-fine eggshell powder per 1 L of the first mixed liquid, evenly stirring for 2 h under a rotational speed of 3500 rpm/min, mixing and obtaining a second mixed liquid containing eggshell powder, lysozyme and chitosan;

(S8) mixing the ultramicroshell membrane powder obtained by the step of (S4) or the shell membrane soluble protein powder obtained by the step of (S5) with the second mixed liquid obtained by the step of (S7) according to a proportion of adding 200 mg of the ultramicroshell membrane powder or the shell membrane soluble protein powder per 1 L of the second mixed liquid, evenly stirring, obtaining a first mixture, adding glycerin 2% volume percentage of the first mixture and xanthan gum 2% volume percentage of the first mixture into the first mixture, magnetically stirring for 2 h under a rotational speed of 3500 rpm/min, evenly mixing and obtaining a mixed solution;

(S9) taking 50 mL of the mixed solution obtained by the step of (S8), evenly dispersing the ultrafine membrane powder or the membrane soluble protein powder in the mixed solution under a continuous ultrasound condition with an intensity of 200 W for 45 min, and obtaining a suspension liquid; and (S10) adding 0.75 mL of the suspension liquid obtained by the step of (S9) into a 12-well plate, horizontally laying, drying at a temperature of 37° C., obtaining a film on the 12-well plate, removing the film from the 12-well plate, storing in a dryer, and obtaining the water resistant enhanced wound healing film and recording as a sample S2.

Third Embodiment

As shown in FIG. 1, a preparation method of a water resistant enhanced wound healing film according to a third embodiment of the present invention is illustrated, wherein the preparation method comprises steps of:

(S1) selecting a fresh egg, cleaning a surface of the fresh egg, removing a content of the fresh egg, and obtaining an eggshell with membrane containing egg white residues;

(S2) washing the eggshell with the membrane containing the egg white residues with a first amount of deionized water according to a proportion of adding 1 mg of the eggshell with the membrane containing the egg white residues per 5 L of the first amount of deionized water, and respectively collecting the eggshell with the membrane and an aqueous solution containing the egg white residues;

(S3) adjusting a pH (potential of hydrogen) value of the aqueous solution containing the egg white residues collected by the step of (S2) to 9 by NaOH (sodium hydroxide) solution with a concentration of 1 mol/L, and then adding 10% of D152-type cation exchange resin, and extracting lysozyme by resin adsorption;

(S4) preliminarily smashing with a pulverizer after drying the eggshell with the membrane collected by the step of (S2), immersing in a second amount of deionized water, mechanically stirring under a rotational speed of 4000 rpm/min for 3 h, standing for 15 min, suspending the membrane in an aqueous phase, sinking the eggshell at a bottom of a beaker due to large density of the eggshell, drying at 50° C. for 24 h after respectively collecting the eggshell and the membrane, respectively ball-milling the eggshell and the membrane into ultrafine powder with a same bore diameter of 10 nm by a ball mill, and respectively obtaining ultra-fine eggshell powder and ultramicroshell membrane powder;

(S5) extracting a soluble mixed protein in the ultramicroshell membrane powder by using thioglycolic acid as a solvent, freeze-drying, and obtaining shell membrane soluble protein powder;

(S6) mixing the lysozyme obtained by the step of (S3) and a chitosan acetic acid solution with a concentration of 3 mg/L according to a proportion of adding 15 mg of the lysozyme per 1 L of the chitosan acetic acid solution, evenly stirring for 10 h in a magnetic stirrer, standing for a period of time, defoaming and obtaining a first mixed liquid containing lysozyme and chitosan;

(S7) mixing the ultra-fine eggshell powder obtained by the step of (S4) and the first mixed liquid obtained by the step of (S6) according to a proportion of adding 5 mg of the ultra-fine eggshell powder per 1 L of the first mixed liquid, evenly stirring for 2 h under a rotational speed of 4000 rpm/min, mixing and obtaining a second mixed liquid containing eggshell powder, lysozyme and chitosan;

(S8) mixing the ultramicroshell membrane powder obtained by the step of (S4) or the shell membrane soluble protein powder obtained by the step of (S5) with the second mixed liquid obtained by the step of (S7) according to a proportion of adding 500 mg of the ultramicroshell membrane powder or the shell membrane soluble protein powder per 1 L of the second mixed liquid, evenly stirring, obtaining a first mixture, adding glycerin 0.05% volume percentage of the first mixture and glucan 0.1% volume percentage of the first mixture into the first mixture, magnetically stirring for 2 h under a rotational speed of 3500 rpm/min, evenly mixing and obtaining a mixed solution;

(S9) taking 50 mL of the mixed solution obtained by the step of (S8), evenly dispersing the ultrafine membrane powder or the membrane soluble protein powder in the mixed solution under a continuous ultrasound condition with an intensity of 300 W for 30 min, and obtaining a suspension liquid; and (S10) adding 0.75 mL of the suspension liquid obtained by the step of (S9) into a 12-well plate, horizontally laying, drying at a temperature of 37° C., obtaining a film on the 12-well plate, removing the film from the 12-well plate, storing in a dryer, and obtaining the water resistant enhanced wound healing film and recording as a sample S3.

Fourth Embodiment

As shown in FIG. 1, a preparation method of a water resistant enhanced wound healing film according to a fourth embodiment of the present invention is illustrated, wherein the preparation method comprises steps of:

(S1) selecting a fresh egg, cleaning a surface of the fresh egg, removing a content of the fresh egg, and obtaining an eggshell with membrane containing egg white residues;

(S2) washing the eggshell with the membrane containing the egg white residues with a first amount of deionized water according to a proportion of adding 1 mg of the eggshell with the membrane containing the egg white residues per 10 mL of the first amount of deionized water, and respectively collecting the eggshell with the membrane and an aqueous solution containing the egg white residues;

(S3) adjusting a pH (potential of hydrogen) value of the aqueous solution containing the egg white residues collected by the step of (S2) to 12 by NaOH (sodium hydroxide) solution with a concentration of 1 mol/L, and then adding 20% of FPC3500-type resin, and extracting lysozyme by resin adsorption;

(S4) preliminarily smashing with a pulverizer after drying the eggshell with the membrane collected by the step of (S2), immersing in a second amount of deionized water, mechanically stirring under a rotational speed of 3500 rpm/min for 4 h, standing for 15 min, suspending the membrane in an aqueous phase, sinking the eggshell at a bottom of a beaker due to large density of the eggshell, drying at 50° C. for 24 h after respectively collecting the eggshell and the membrane, respectively ball-milling the eggshell and the membrane into ultrafine powder with a same bore diameter of 1000 nm by a ball mill, and respectively obtaining ultra-fine eggshell powder and ultramicroshell membrane powder;

(S5) extracting a soluble mixed protein in the ultramicroshell membrane powder by using mercaptopropionic acid as a solvent, freeze-drying, and obtaining shell membrane soluble protein powder;

(S6) mixing the lysozyme obtained by the step of (S3) and a chitosan acetic acid solution with a concentration of 5 mg/L according to a proportion of adding 10 mg of the lysozyme per 1 L of the chitosan acetic acid solution, evenly stirring for 10 h in a magnetic stirrer, standing for a period of time, defoaming and obtaining a first mixed liquid containing lysozyme and chitosan;

(S7) mixing the ultra-fine eggshell powder obtained by the step of (S4) and the first mixed liquid obtained by the step of (S6) according to a proportion of adding 10 mg of the ultra-fine eggshell powder per 1 L of the first mixed liquid, evenly stirring for 2 h under a rotational speed of 5000 rpm/min, mixing and obtaining a second mixed liquid containing eggshell powder, lysozyme and chitosan;

(S8) mixing the ultramicroshell membrane powder obtained by the step of (S4) or the shell membrane soluble protein powder obtained by the step of (S5) with the second mixed liquid obtained by the step of (S7) according to a proportion of adding 50 mg of the ultramicroshell membrane powder or the shell membrane soluble protein powder per 1 L of the second mixed liquid, evenly stirring, obtaining a first mixture, adding glycerin 5% volume percentage of the first mixture and carboxymethyl cellulose 5% volume percentage of the first mixture into the first mixture, magnetically stirring for 2 h under a rotational speed of 3500 rpm/min, evenly mixing and obtaining a mixed solution;

(S9) taking 50 mL of the mixed solution obtained by the step of (S8), evenly dispersing the ultrafine membrane powder or the membrane soluble protein powder in the mixed solution under a continuous ultrasound condition with an intensity of 400 W for 30 min, and obtaining a suspension liquid; and (S10) adding 0.75 mL of the suspension liquid obtained by the step of (S9) into a 12-well plate, horizontally laying, drying at a temperature of 37° C., obtaining a film on the 12-well plate, removing the film from the 12-well plate, storing in a dryer, and obtaining the water resistant enhanced wound healing film and recording as a sample S4.

First Comparative Example

Take a film, prepared by using simple chitosan as a raw material, as a comparative sample. The preparation method of the film comprises steps of:

(S1) adding commercially available chitosan powder into an acetic acid solution according to a weight concentration (w/v) of 1 mg/L, stirring in a magnetic stirrer for 10 h, standing for a period of time, defoaming, and obtaining a first mixed liquid containing the chitosan and the acetic acid;

(S2) adding 1% of glycerin by volume percentage of the first mixed liquid and 2% of carboxymethyl cellulose by volume percentage of the first mixed liquid into the first mixed liquid, magnetically stirring for 2 h under a rotational speed of 3500 rpm/min, evenly mixing and obtaining a mixed solution; and (S3) horizontally laying after adding 0.75 mL of the mixed solution obtained by the step of (S2) into a 12-well plate, drying at a temperature of 37° C., obtaining a film on the 12-well plate, removing the film from the 12-well plate, storing in a dryer, and obtaining the film and recording as a sample D1.

The physical properties, pH value, degradation rate, water resistance and ability to inhibit microbial growth of the wound healing film samples S1 to S4 respectively obtained by the above first, second, third and fourth embodiments, and the simple chitosan sample D1 obtained by the above comparative example were compared as follows:

(1) Water Resistance Test:

The sample S3 and the sample D1 are selected and tested as follows.

(a) The sample S3 of the present invention and the simple chitosan membrane sample D1 are respectively immersed in a wound simulating solution, and then the integrity of the samples is observed after 24 h.

(b) The sample S3 of the present invention and the simple chitosan membrane sample D1 are respectively immersed in normal saline, and then the integrity of the samples is respectively observed after 1 day, 2 days and 3 days.

As shown in FIGS. 2a and 2b, it can be seen from the sensory analysis, the comparative sample D1 has a softening (melting) feeling, while the sample S3 is relatively tough, complete and exhibits good transparency.

FIGS. 3-1a, 3-1b, 3-2a, 3-2b, 3-3a and 3-3b are appearance patterns of the simple chitosan film sample D1 in the comparative example and the water resistant enhanced wound healing film sample S3 provided by the present invention after being immersed in normal saline for 1, 2 and 3 days, respectively, which indicates that the wound healing film sample S3 provided by the present invention has better integrity and water resistance than the simple chitosan film sample D1.

(2) Degradation Rate Test:

The simple chitosan film sample D1 and the samples S1-S4 are respectively cut to a same size of 12 mm×12 mm, are respectively weighed, and recorded as an initial film weight ($W_0$); and then are immersed in a sealed beaker containing lysozyme and PBS (phosphate buffer saline) buffer solution in accordance with a proportion of 1 mg/mL at 37° C. for a period of time. Different periods are selected, and then the excess moisture on the surface of the films is absorbed by filter paper, and finally the wet weight of the films is tested and recorded as Wi. Accordingly, the test formula of the degradation rate is expressed as:

$$Wu(\%) = \left(\frac{Wi}{W0} - 1\right) \times 100\%.$$

Degradation rates at different periods are drawn, as shown in FIG. 4. The samples begin to degrade from 1 h. The degradation speed of the sample D1 is significantly higher than that of the samples S1 to S4. After degradation for 96 h (4 days), the degradation rates of the wound healing film samples 51 to S4 are significantly lower than the degradation rate of the simple chitosan film sample D1, and particularly, the degradation rates (about 20%) of the samples S2 and S3 are lowest and far below the degradation rate (70%) of the simple chitosan film sample D1.

(3) Absorption Rate Test of Bovine Serum Albumin:

30 mg of the simple chitosan film sample fragments D1 and the sample fragments S1-S4 are respectively selected and placed in a 24-well plate, immersed in a PBS buffer solution for 2-3 h, placed in 0.75 mL of the bovine serum albumin solution with a concentration of 10 mg/L and cultured for 24 h. The protein concentration in the bovine serum albumin solution before and after the fragments are immersed by a microplate reader is tested. Through the protein concentration difference before and after the fragments are immersed, the ability of the film to absorb bovine serum albumin is determined.

Figure 5:
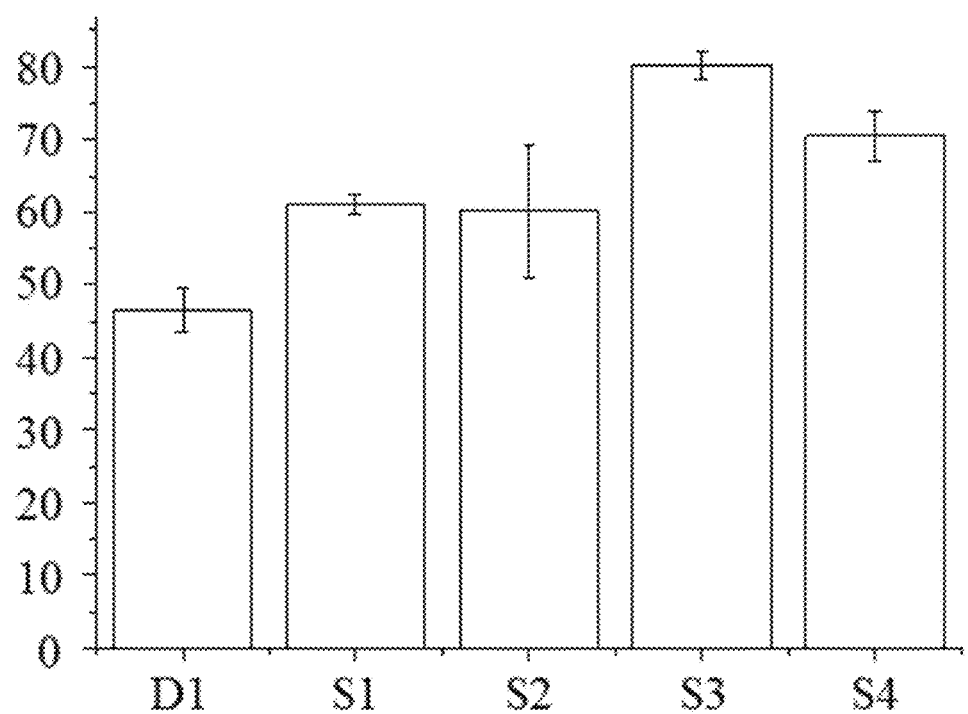
FIG. 5 is a column chart of bovine serum albumin absorption rate of the simple chitosan film sample D1 in the comparative example and the water resistant enhanced wound healing film samples S1-S4 provided by the present invention.

As shown in FIG. 5, the bovine serum albumin absorption rate (60 mg/g-80 mg/g) of the water resistant enhanced wound healing film samples S1-S4 provided by the present invention is much higher than that of the simple chitosan film sample D1 (46 mg/g) in the comparative example, and particularly, the bovine serum albumin absorption rate of the water resistant enhanced wound healing film sample S3 is best and 80 mg/g.

(4) pH Test:

At room temperature, the simple chitosan film sample D1 and the sample fragments S1-S4 are immersed and cultured in normal saline for 24 h, and then a pH value of an immersing solution is tested by a pH meter.

Figure 6:
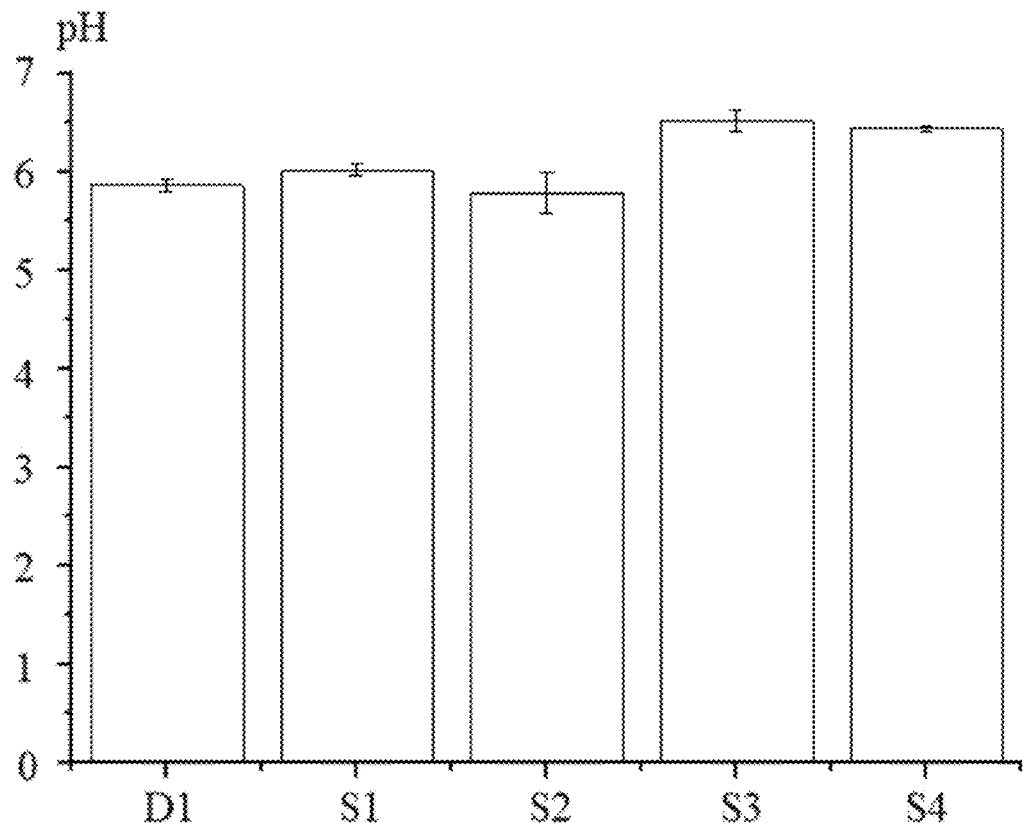
FIG. 6 is a column chart of pH value of the simple chitosan film sample D1 in the comparative example and the water resistant enhanced wound healing film samples S1-S4 provided by the present invention.

As shown in FIG. 6, pH values of the film samples S1-S4 and the simple chitosan film sample D1 in normal saline are weakly acidic to provide a suitable microenvironment for wound healing.

(5) Bacteriostatic Test:

The simple chitosan film sample D1 and the samples S1-S4 after sterilization are immersed in 1.5 mL of diluted bacterial solution which contains *E. coli* and *Staphylococcus aureus*. An initial OD (optical density) of the bacterial solution is 0.07. A bacterial solution having a same dilution ratio without membrane immersion is used as the control group, and cultured at 37° C. for 24 h. And then under sterile conditions, 200 μL of the bacterial solution is taken, and the turbidity of the bacterial solution is tested by a microplate reader. The OD value represents the turbidity of the bacterial solution. The higher the OD value, the lower the concentration of bacteria after 24 hours of culture, and the stronger the bacteriostatic effect of the film.

Figure 7:
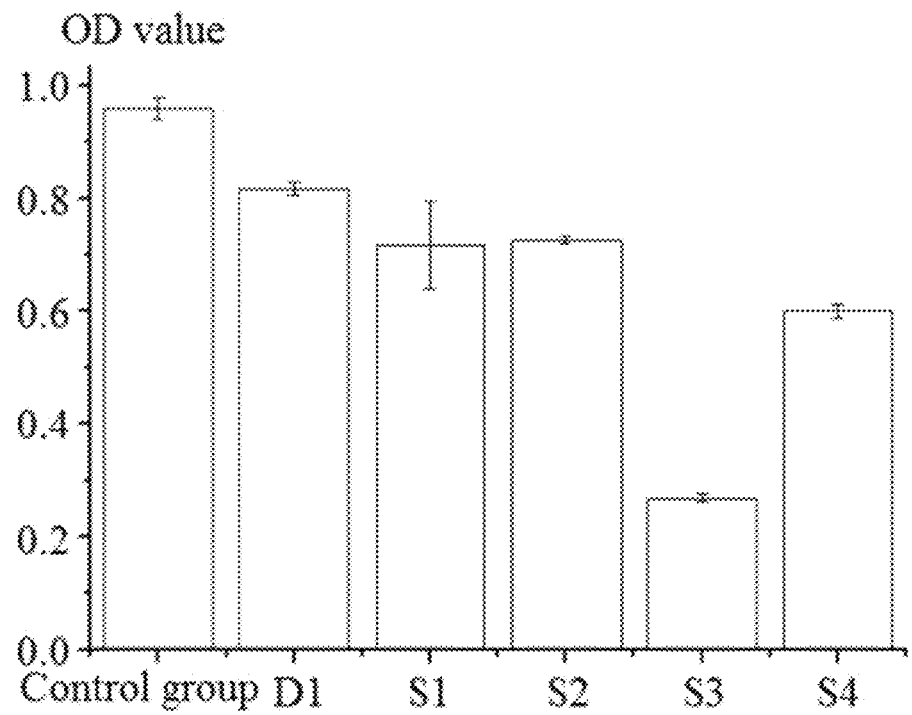
FIG. 7 is a column chart of growth inhibition of *Escherichia coli* of the simple chitosan film sample D1 in the comparative example and the water resistant enhanced wound healing film samples S1-S4 provided by the present invention.
Figure 8:
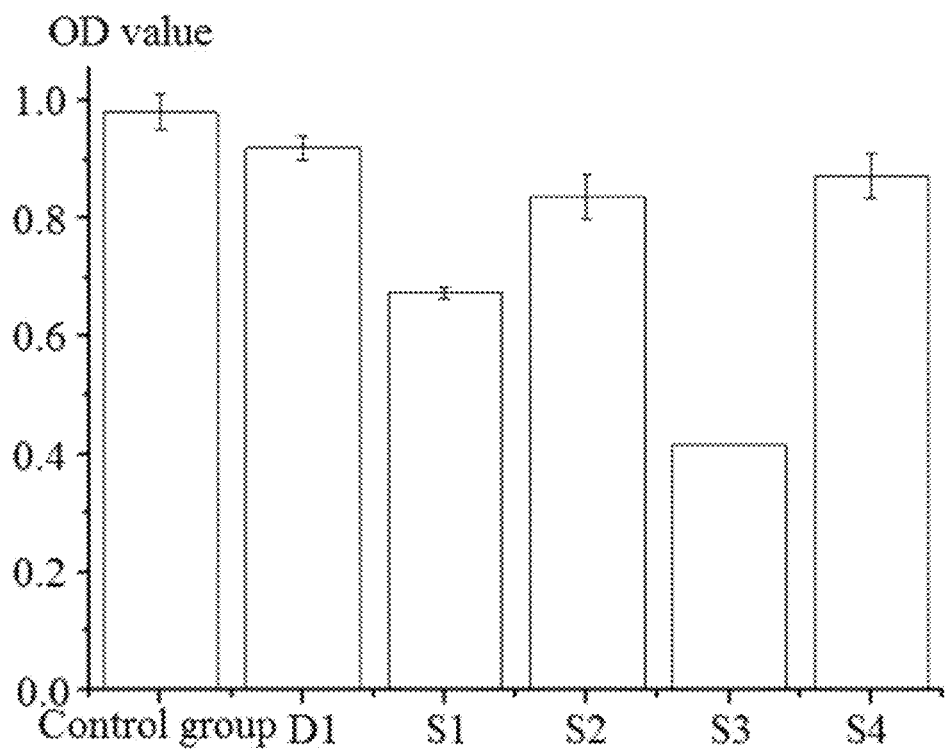
FIG. 8 is a column chart of growth inhibition of *Staphylococcus aureus* of the simple chitosan film sample D1 in the comparative example and the water resistant enhanced wound healing film samples S1-S4 provided by the present invention.

The experimental results are shown in FIGS. 7 and 8. As shown in FIG. 7, the turbidity of the *E. coli* solution after the water resistant enhanced wound healing film samples S1-S4 provided by the present invention are immersed is obviously lower than that of the control group and the simple chitosan film sample D1, which indicates that the samples S1-S4 of the present invention have good inhibition to *E. coli*, and especially the sample S3 has the lowest turbidity and the best bacteriostatic activity.

As shown in FIG. 8, the turbidity of the *E. coli* and *Staphylococcus aureus* solution after the water resistant enhanced wound healing film samples S1-S4 provided by the present invention are immersed is obviously lower than that of the control group and the simple chitosan film sample D1, which indicates that the samples S1-S4 of the present invention have good bacteriostatic activity, and especially the sample S3 has the lowest turbidity and the best bacteriostatic activity.

In summary, compared with the film prepared by using simple chitosan as a raw material, the water resistant enhanced wound healing film provided by the present invention, which uses high-molecular polymer, eggshell membrane and chitosan as raw materials, has advantages as follows.

(1) The wound healing film provided by the present invention has a certain water resistance and mechanical properties. For example, after being immersed in wound simulated liquid (salt saline) for 1 to 3 days, the wound healing film provided by the present invention still have a complete appearance.

(2) The wound healing film provided by the present invention has good physical appearance, such as good flexibility, folding resistance and transparency.

(3) The wound healing film provided by the present invention has good protein absorption capacity. For example, bovine serum albumin absorption rate is in a range of 60 mg/g-80 mg/g which is significantly higher than the simple chitosan absorption rate of 40 mg/g.

(4) The wound healing film provided by the present invention can greatly reduce the degradation rate of the dressing and shorten the healing time of the dressing.

(5) The wound healing film provided by the present invention provides a suitable pH for rapid wound healing and creates a microenvironment for wound healing.

(6) The wound healing film provided by the present invention can significantly inhibit the growth of *Escherichia coli* and *Staphylococcus aureus*. By inhibiting the growth of microorganisms, the dressing can effectively prevent the microorganisms from infecting wounds so as to improve the speed of wound healing.

Since the eggshell and shell membrane of chicken eggs, duck eggs, quail eggs or goose eggs are basically the same, the present application does not list and describe them again. The above scheme and conclusions about egg shells are suitable for the corresponding duck eggs, quail eggs or goose eggs.

The above are some specific embodiments of the present invention, but it should not be construed as limiting the present invention. Therefore, it should be noted that any modification and improvement based on the present invention falls within the protective scope of the present invention.

What is claimed is:

1. A water resistant enhanced wound healing which comprises components by mass to volume at concentrations of:
   (i) ultra-fine eggshell powder—5-10 mg/L;
   (ii) shell membrane soluble protein—50-500 mg/L;
   (iii) lysozyme—5-30 mg/L;
   (iv) chitosan—5-10 mg/L;
   (v) glycerin—0.05-5 mg/L, and
   (vi) a polysaccharide polymer—0.1-5 mg/L.

2. The water resistant enhanced wound healing film, as recited in claim 1, wherein the ultra-fine eggshell powder is made from chicken eggs and the shell membrane soluble protein is made from chicken eggs.

3. The water resistant enhanced wound healing film, as recited in claim 1, wherein the polysaccharide polymer is a mixture of xanthan gum and dextran.

4. A method of making the water resistant enhanced wound healing film of claim 1, wherein the method comprises the steps of:
   (S1) selecting a fresh egg, cleaning a surface of the fresh egg, removing a content of the fresh egg, and obtaining an eggshell with membrane containing egg white residues;
   (S2) washing the eggshell with the membrane containing the egg white residues with a first amount of deionized water, and respectively collecting the eggshell with the membrane and an aqueous solution containing the egg white residues;
   (S3) adjusting a pH (potential of hydrogen) value of the aqueous solution containing the egg white residues collected by the step of (S2) to a range of 6-12 with acid or alkali, extracting the aqueous solution by passing it over an adsorption resin, and obtaining lysozyme;
   (S4) drying the eggshell with the membrane collected by the step of (S2), preliminarily grinding it with a pulverizer, immersing it in a second amount of deionized water, stirring it and mechanically separating the eggshell from the membrane, respectively collecting the eggshell and the membrane by their different densities, grinding the eggshell and the membrane, and obtaining ultra-fine eggshell powder and shell membrane powder;
   (S5) extracting a soluble protein mixture from the shell membrane powder by using any one of mercaptopropionic acid, thioglycolic acid or acetic acid as a solvent, freeze-drying, and obtaining shell membrane soluble protein powder;
   (S6) mixing the lysozyme obtained by the step of (S3) and a chitosan-acetic acid solution with a concentration in a range of 1-5 mg/L according to a proportion of adding 5 mg to 30 mg of the lysozyme per 1 L of the chitosan-acetic acid solution, e stirring, and obtaining a first mixed liquid containing lysozyme and chitosan;
   (S7) mixing the ultra-fine eggshell powder obtained by the step of (S4) and the first mixed liquid Obtained by the step of (S6) according to a proportion of adding 5 mg to 30 mg of the ultra-fine eggshell powder per 1 L of the first mixed liquid, evenly stirring, and obtaining a second mixed liquid containing eggshell powder, lysozyme and chitosan;
   (S8) mixing the shell membrane powder obtained by the step of (S4) or the shell membrane soluble protein powder obtained by the step of (S5) with the second mixed liquid obtained by the step of (S7) according to a proportion of adding 50 mg to 500 mg of the shell membrane powder or the shell membrane soluble protein powder per 1 L of the second mixed liquid, evenly stirring, obtaining a first mixture, adding glycerin in an amount of 0.05% to 5% by volume percentage of the first mixture and a polysaccharide polymer in an amount of 0.1% to 5% by volume percentage of the first mixture, both into the first mixture, evenly stirring, and obtaining a mixed solution;
   (S9) taking the mixed solution obtained by the step of (S8), evenly dispersing the shell membrane powder or the shell membrane soluble protein powder in the mixed solution by ultrasound, and obtaining a liquid suspension, and
   (S10) adding 1.5 ml of the suspension liquid obtained by the step of (S9) into a well plate, laying horizontally, drying it at a temperature in a range of 25 to 50° C., Obtaining a film, removing the film from the well plate, drying and storing it, and obtaining the water resistant enhanced wound healing film.

5. The preparation method of the water resistant enhanced wound healing film, as recited in claim 4, wherein the alkali in the step of (S3) for adjusting the pH value is sodium hydroxide or potassium hydroxide.

6. The preparation method of the water resistant enhanced wound healing film, as recited in claim 4, wherein the adsorption resin in the step of (S3) is a cation exchange resin, and the amount of the adsorption resin is 0.1%-20% w/v.

7. The preparation method of the water resistant enhanced wound healing film, as recited in claim 5, wherein the adsorption resin in the step of (S3) is a cation exchange resin, and the amount of the adsorption resin is 0.1%-20% w/v.

8. The preparation method of the water resistant enhanced wound healing film, as recited in claim 4, wherein in the step of (S8), the polysaccharide polymer is at least one member selected from the group consisting of carboxymethyl cellulose, xanthan gum and dextran.

9. The preparation method of the water resistant enhanced wound healing film, as recited in claim 5, wherein in the step of (S8) the polymer polysaccharide is at least one member selected from the group consisting of carboxymethyl cellulose, xanthan gum and dextran.

10. The preparation method of the water resistant enhanced wound healing film, as recited in claim 4, wherein
   (a) in the step of (S4), the eggshell is mechanically separated from the membrane by centrifugation at a rotational speed in a range of 2000 to 6000 rpm/min for 2-4 h;
   (b) in the step of (S6), the first mixed liquid is obtained by stirring with a magnetic stirrer for 6-15 h; and
   (c) in the step of (S7), the second mixed liquid is obtained by stirring at a rotational speed in a range of 2000 to 5000 rpm/min for 1-5 h.

11. The preparation method of the water resistant enhanced wound healing film, as recited in claim 5, wherein
   (a) in the step of (S4), the eggshell is mechanically separated from the membrane by centrifugation at a rotational speed in a range of 2000 to 6000 rpm/min for 2 h;
   (b) step of (S6), the first mixed liquid is obtained by stirring with a magnetic stirrer for 6-15 h; and
   (c) in the step of (S7), the second mixed liquid is obtained by stirring at a rotational speed in a range of 2000 to 5000 rpm/min for 1-5 h.

12. The preparation method of the water resistant enhanced wound healing film, as recited in claim 4, wherein in the step of (S9), the ultrasound is continuous ultrasound or intermittent ultrasound with an ultrasonic intensity in a range of 100 to 400 W and an ultrasonic time in a range of 30 to 60 min.

* * * * *